United States Patent [19]
Lerman

[11] Patent Number: 5,088,489
[45] Date of Patent: * Feb. 18, 1992

[54] CURRENT-BASED DEFIBRILLATING METHOD

[76] Inventor: Bruce B. Lerman, 450 E. 63rd St., Apt. 3N, New York, N.Y. 10021

[*] Notice: The portion of the term of this patent subsequent to Sep. 20, 2005 has been disclaimed.

[21] Appl. No.: 211,871

[22] Filed: Jun. 27, 1988

Related U.S. Application Data

[63] Continuation-in-part of Ser. No. 915,080, Oct. 3, 1986, Pat. No. 4,771,781.

[51] Int. Cl.$^5$ .............................................. A61N 1/39
[52] U.S. Cl. ..................................... 128/419; 128/734
[58] Field of Search ............................ 128/419 D, 734

[56] References Cited

U.S. PATENT DOCUMENTS

| | | | |
|---|---|---|---|
| 3,782,389 | 1/1974 | Bell | 128/419 D |
| 3,860,009 | 1/1975 | Bell et al. | 128/419 D |
| 3,862,636 | 1/1975 | Bell et al. | 128/419 D |
| 3,886,950 | 6/1975 | Ukkestad et al. | 128/419 D |
| 4,328,808 | 5/1982 | Charbonnier et al. | 128/419 D |
| 4,574,810 | 3/1986 | Lerman | 128/734 |
| 4,578,635 | 3/1986 | Mee et al. | 128/419 D |
| 4,840,177 | 6/1989 | Charbonnier et al. | 128/734 |

FOREIGN PATENT DOCUMENTS 0612331  6/1978  U.S.S.R. ................................ 128/908

OTHER PUBLICATIONS

Determining Transthoracic Impedance, Delivered Energy, and Peak Current During Defibrillation Episodes. By V. C. Jones, M.S., F. N. Charbonnier, Ph.D., P. Long, B.S., *Medical Instrumentation*, vol. 15, No. 6, Nov.-Dec. 1981, 380-382.

Relationship Between Canine Transthoracic Impedance and Defibrillation Threshold. By Lerman, Halperin, Tsitlik, Brin, Clark and Deale, The American Society for Clinical Investigation, Inc. vol. 80, Sep. 1987, 797-803.

Advanced Prediction of Transthoracic Impedance in Human Defibrillation and Cardioversion: Importance of Impedance in Determining the Success of Low-Energy Shocks, By Kerber, Kouba, Martins, Kelly, Low, Hoyt, Ferguson, Bailey, Bennett, Charbonnier—Circulation 70, No. 2, 303-308, 1984.

Accurate Isolated and Microprocessor—Controlled Current Source for a Wide Range of Applications. By Goovaerts and Meekes Medical & Biological Engineering & Computing, Jul. 1981, 491-496.

Current Density and Electricallhy Induced Ventricular Fibrillation, By Starmer and Whalen, Medical Instrumentation, vol. 70, Jan.-Feb. 1973, 3-4.

Current-Based Defibrillation: An Improved Method of Ventricular Defibrillation. By Bruce B. Lerman, M.D., et al. Dept. of Med., Div. of Cardiology, Univ. of Va. Medical Center, Charlottesville, Va.

Ventricular Defibrillation Thresholds with Capacitor Discharge. By Armayor et al. Med. & Biol. Eng. and Comput. 1979, vol. 17, pp. 435-442.

Automated Impedance-Based Energy Adjustment for Defibrillation: Circulation, vol. 71, No. 1, Jan., 1985.

Effects of Energy Delivery Via a His Bundle Catheter during closed Chest ablation of the Atrioventricular Conduction System. By Trantham et al., Journal of Clinical Investigation; vol. 72, 1562-1574, 1983.

The Production of the Impedance of the Thorax to Defibrillating Current. By L. A. Geddes, et al.

Cardiac Capacitive Defibrillator Controlled by Tiristor. By Savino, et al.

Defibrilador Cardiaco de Forma De Onda Variable Controlado a Tiristor, By Guillermo Vicente Savino.

*Primary Examiner*—William E. Kamm
*Assistant Examiner*—Scott M. Getzow
*Attorney, Agent, or Firm*—Walter G. Marple, Jr.

[57] ABSTRACT

An apparatus and method for the treatment of ventricular fibrillation, ventricular tachycardia, or supraventricular tachycardia. The method being to prospectively ascertain a patient's transthoracic resistance by application of a low amplitude current via the apparatus electrodes applied to a patient's chest, charging a capacitor of the apparatus sufficiently for delivery of a minimal peak current, e.g., 25 amperes for treatment of ventricular fibrillation preselected by the operator as appropriate for attaining defibrillation, and the capacitor is discharged through the electrodes to effect the defibrillation. The apparatus can be made by modifying conventional direct current defibrillator devices.

9 Claims, 2 Drawing Sheets

CURRENT-BASED DEFIBRILLATING METHOD

This is a continuation in-part of application Ser. No. 915,080 filed Oct. 3, 1986, now U.S. Pat. No. 4,771,781 as issued Sept. 20, 1988.

BACKGROUND OF THE INVENTION

Widespread use of DC defibrillators in patients suffering cardiac arrest has greatly increased the rate of successful resuscitation both in and out of hospitals over the past few decades. Defibrillation is applicable to life-threatening cardiac arrests resulting from ventricular fibrillation which occurs because of asynchronous depolarization of cardiac cells. When a sufficient electrical pulse is delivered to the heart from an external defibrillator through a set of paddles (electrodes), all cardiac cells briefly arrest and thereafter synchronous or normal depolarization may once again resume.

The defibrillator equipment presently offered to the medical arts discharges the electrical energy through an RLC circuit which is manually triggered by the physician, and the heretofore standard quantity of the electrical pulse to be delivered has been calibrated in terms of joules of energy. The many studies reported in the medical literature of attempts to determine the optimal electrical strength of the pulse that should be delivered for defibrillation are almost invariably analyzed in terms of joules. Delivery of more than enough electrical energy for defibrillation has been associated with cardiac cell death, yet insufficient energy will not accomplish the desired defibrillation, resulting then in multiple attempts to defibrillate at ever higher energy levels.

Previous recommendations for the "first attempt" defibrillation usually have been based on gross energy levels e.g., 200 joules. In fact, according to the STANDARDS AND GUIDELINES FOR CARDIOPULMONARY RESUSCITATION (CPR) AND EMERGENCY CARDIAC CARE (ECC)—published in JAMA, Vol. 225, pp 2942-2943, 1986, patients in ventricular fibrillation should receive DC countershocks of 200 joules (first shock), 200 joules (second shock), and 360 joules (third shock), as needed.

Selection of energy dose level for threshold defibrillation is believed to be sub-optimal for several reasons. For a given pulse duration, peak current is a better predictor of the defibrillation threshold than delivered energy. Lerman et al., "Relationship between Canine Transthoracic Impedance and Defibrillation Threshold: Evidence for Current-based Defibrillation." Journal of Clinical Investigation, Vol. 80, pp. 797-803, Sept., 1987). Establishment of the defibrillation pulse on the basis of total electrical energy, as has been done by prior workers in the art, does not apply a consistent level of peak current (amperage) because, in humans as well as dogs, transthoracic resistance varies within large ranges from one subject to the next. The implication of these findings is that defibrillation doses should be calibrated in units of (or at least based upon) current instead of energy.

An object of this invention is to provide a method and apparatus for automatically providing a preselected threshold level of peak current adequate for defibrillation, wherein the defibrillator capacitor is charged according to the transthoracic resistance of each patient in order to provide the selected peak current.

Additionally, it is an object of the invention to prospectively determine such transthoracic resistance automatically and prior to defibrillation by applying to the patient a low amplitude exploration current via the defibrillator electrodes.

Further objects of the invention and the advantages thereof will become apparent from the description which follows.

RATIONALE OF THE INVENTION

Although it has been customary in the defibrillator art to apply electrical energy as such, i.e., a pulse denominated in joules, some workers in the art have appreciated that delivered current is better than discharged energy as a measurement of a defibrillating threshold, as for example in U.S. Pat. No. 3,862,636, wherein the magnitude of the current delivered to the patient was varied in accordance with the body weight of the patient.

Other recent art has recognized that total energy may not be the most adequate electrical parameter to describe the dose for defibrillation, urging that the peak current level per heart weight or body weight might be the best descriptor of the energy needed to depolarize some critical mass of cells and achieve successful defibrillation, (in the instance of canine hearts at least). See, for example, Armayor et al. "Ventricular Defibrillation Threshholds with Capacitor Discharge", Med. & Biol. Eng. and Comput. 1979, Vol. 17, pp. 435-442.

Kerber, et al., "Automated Impedance-Based Energy Adjustment for Defibrillation: Experimental Studies", Circulation, Vol. 71, No. 1, January 1985, suggest automatic increases of energy in arbitrary amounts, from an operator-selected energy level, when prospected transthoracic resistance exceeds a mean level based on previously observed patients. U.S. Pat. No. 3,860,009 computes a peak defibrillation current based on energy and transthoracic resistance or body weight and delivers the energy by discharge of capacitors directly into the resistance load of the patient resulting in an approximately ramp voltage RC discharge pulse output.

The gist of the above-noted art is that a need exists for identifying patients with such high transthoracic resistance that application of relatively low energy, e.g., 100 joules, defibrillation shock levels are unlikely of success.

The inventor hereof, in U.S. Pat. No. 4,574,810, suggested that such an approach was too gross, and that a superior approach would be to ascertain a threshold level of peak current based on the requirements of each patient, and then to apply whatever electrical energy would result in the desired level of peak current. Further, a resistance measuring system was associated with the defibrillator circuitry and the electrical shock energy administered by the defibrillator was controlled according to measured transthoracic resistance to provide a predetermined amount of peak defibrillation current per calculated ohm of resistance.

In laboratory studies using canines, defibrillation thresholds were determined by the inventor at two different transthoracic resistances, the resistance being altered by changing electrode area or by change in electrode force. Under the conditions of this study, it was found that threshold defibrillation current was independent of the transthoracic resistance for a given dog and was invariant for a given animal whereas, in contrast, energy and voltage thresholds showed large variability. These results suggest that redefining defibrillation threshold in terms of peak current rather than energy provides a superior method of defibrillation (Lerman, et al., "Relationship between Canine Transthoracic Impedance and Defibrillation Threshold: Evidence for Current-based Defibrillation," Journal of Clinical Investigation, Vol. 80, pp. 797-803, September, 1987).

To test the hypothesis that a current-based defibrillation method (vide infra) would result in delivering less energy and peak current than the standard energy-based method, the inventor hereof conducted a study in which eighty-six (86) patients in ventricular fibrillation were prospectively randomized to receive either DC countershocks according to the above-noted energy-based guidelines (200 J, first and second shocks, 360 J, third shock) or to receive current-based shocks of 25 amperes (first shock), 25 amperes (second shock), and 40 amperes (third shock), by a modified defibrillator, as needed. Patients randomized to each method were similar with respect to age, sex, cardiac diagnosis, weight, ejection fraction, physical parameters and transthoracic resistance. Each method had statistically equivalent first shock (79% current-based versus 81% energy-based) and cumulative shock success rates. The mean ($\pm$SD) first shock energy for patients receiving the current-based method was 120$\pm$30 J and 200 J for patients receiving energy-based shocks, p=0.0001. The mean peak current was 24$\pm$2.3 A and 33$\pm$5.0 A, respectively, p=0.0001. Therefore, for equivalent first shock success rates, the energy-based method delivered 67% more energy and 38% more current. High transthoracic resistance (>90 ohms) predicted first shock failure only in patients defibrillated by the energy-based defibrillating method. These findings suggest that the current-based defibrillating method precludes transthoracic resistance as a major determinant of defibrillation success and delivers significantly less current and energy than the standard energy-based method for an equivalent success rate.

BRIEF STATEMENT OF THE INVENTION

Briefly stated, the defibrillator of this invention automatically determines transthoracic resistance, and then uses the thus-obtained resistance to calculate and charge a capacitor to the level of voltage necessary to deliver an amount of peak current preselected by the operator, an inductance, resistance, capacitance (RLC) discharge pulse delivers that selected peak current. This method of defibrillation is applicable to standard defibrillators used from transthoracic defibrillation and to the Automatic Implantable Cardcoverter-Defibrillator.

After the defibrillating electrodes are in place on a patient's chest, a low amplitude, sinusoidal pulse (or a rectangular pulse of low frequency, such as 31 kHz) is transmitted through the electrodes and a microprocessor is used to calculate the transthoracic resistance in order that a selected value of peak amperage may be delivered to this subject by the defibrillator. The extreme rapidity of electrical measurements, and the rapid response of electrical circuits to control signals are advantageous, since ventricular fibrillation is of life threatening urgency and brooks no delay.

The selected peak defibrillation current to be applied to the patient and the prospected transthoracic resistance are used to control the charge applied to the capacitor of the defibrillator, so that upon discharge of the capacitor, the selected level of peak current desired for defibrillation will result. The charge may be calculated by second order source free RLC equations (Trantham et al., Journal of Clinical Investigation, Vol. 72, 1562-1574, 1983).

Electrical components and circuitry known to the art may be employed in practice of the invention. For example, in practice of the invention, standard microprocessors may be adapted to calculate, transthoracic resistance from a preshock low amplitude current and the electrode-to-electrode voltage developed responsive thereto and to generate the selected level of peak defibrillation current.

Suitably, the microprocessor generates a digital signal for visual readout and recording and, in addition, conversion to an analog form for direct control over the charge being placed on the capacitor of the defibrillator.

Desirably, the peak current subsequently delivered to the patient by the defibrillator, and the voltage between the electrodes are digitized to generate signals which are fed into the microprocessor which, in turn, computes the transthoracic resistance encountered by the defibrillation pulse. The microprocessor then provides appropriate signals for visual readout and recording. If more than one shock is required during an episode of ventricular fibrillation, the transthoracic resistance determined during the immediate preceding defibrillation attempt and the selected peak current will be used to control the charge stored in the capacitor of the defibrillator, so that upon discharge of the capacitator, the selected level of peak current desired for defibrillation will result. For future defibrillation of the same and other patients, it is important to know the degree to which the level of peak current actually delivered by the defibrillator pulse relates to the previously selected peak current level and how transthoracic resistance during defibrillation relates to the patient's resistance measured by the low amplitude exploration current. Given sufficient experiences, a virtually exact predictability for delivered peak current should result, since appropriate adjustments can be made in multiplication factors programmed into the microprocessor.

DISCUSSION OF THE INVENTION

Mention has been made that defibrillation art has concerned itself with measurement of transthoracic resistance and, as might be expected, some suggestions heretofore made to the art are capable of use in practice of this invention, over and above the particular mode hereinafter described. For example, reference is made to "Determining Transthoracic Impedance, Delivered Energy, and Peak Current During Defibrillation Episodes" by Jones et al. in Medical Instrumentation, Vol. 15, No. 6, November-December 1981, pp. 380-382, and, to Kerber et al. "Advanced Prediction of Transthoracic Impedance in Human Defibrillation and Cardioversion: Importance of Impedance in Determining the Success of Low Energy Shocks," Circulation, Vol. 70, pp. 303-308, 1984.

Important to the practice of this invention, of course, is a consonance of the transthoracic resistance as measured by the low amplitude exploration pulse to the transthoracic resistance under defibrillation pulse circumstances. In this connection, it is noted that Kerber, et al. reported that their predicted resistance correlated very well with defibrillation pulse resistance, and such correlation resulted when practice of this invention advanced from animal model results obtained in the genesis of this invention to clinical studies.

Through practice of this invention, the physician may apply a defibrillating shock which should be adequate without being excessive, i.e., be close to the threshold. When using defibrillators calibrated for energy level selections, practice of this invention will automatically identify patients at the extremes of the 25-150 ohm range of human transthoracic resistance for whom a 200 joule defibrillator shock may be either far too low or excessively high and automatically will cause calculation of the energy level needed to apply a defibrillator shock that delivers the selected level of peak current more appropriate to the patient. Preliminary data also indicate that most humans will be successfully defibrillated with a peak delivered current of 25 amperes.

The conceptual framework for practice of this invention involves selecting a desired amount of peak delivered current, i.e., 25 amperes, by the operator; prospectively and automatically determining transthoracic resistance of each patient by application of a low energy, high frequency pulse; then automatically charging the defibrillator capacitor to the voltage level sufficient for delivery of the selected level of peak current transthoracically on discharge; and automatically discharging the capacitor for defibrillating upon attaining such voltage level. All of the steps—from measurement through discharge—are performed with the electrodes on the patient.

Additionally, the voltage developed between electrodes applied to the chest of the patient during the defibrillation shock and the peak current supplied by discharge thereof, may be measured so as to compute and display the transthoracic resistance of the patient during defibrillation discharge and may be used to calculate the capacitor voltage necessary to deliver the selected peak current on subsequent shocks) if needed.

As pointed out by Jones et al., supra, knowledge of the internal circuit parameters peculiar to each defibrillator mode enables normalizing of the peak discharge current. Although not specifically included in the following description of the exemplary embodiment of this invention, normalization for circuit components (internal resistance) in the defibrillator is contemplated, including normalization for add-on internal circuit parameters such as those of the current sensing transformers; and the method and apparatus of the instant invention should be considered as inclusive of performing such normalization whenever desirable. The details of normalization described by Jones et al. supra are incorporated by reference herein as exemplary modes of normalization contemplated herein.

BRIEF DESCRIPTION OF THE DRAWINGS

For further understanding of this invention, reference is made to the attached drawing wherein.

DETAILED DESCRIPTION OF THE INVENTION

Figure 1:
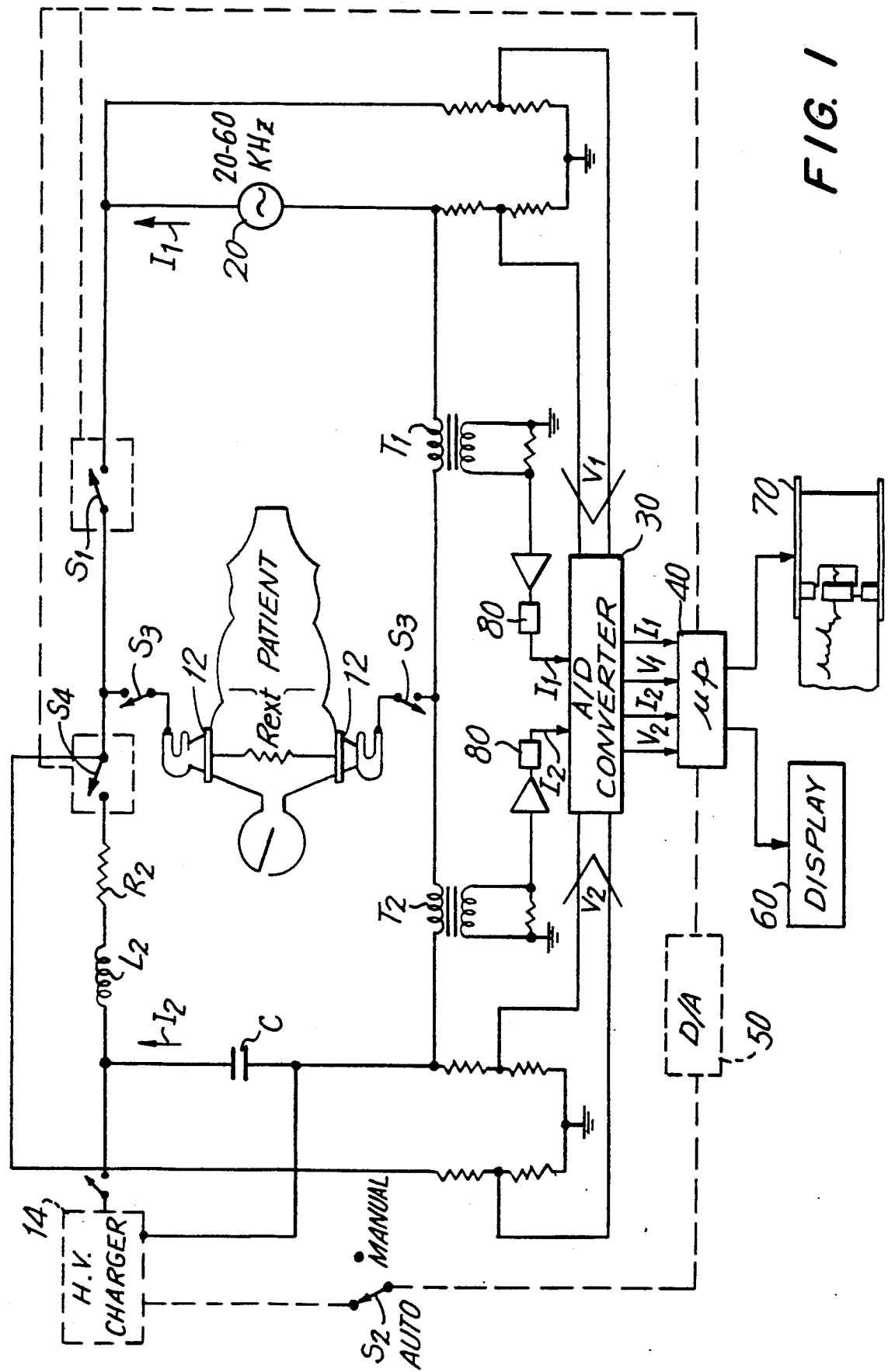
FIG. 1 is a schematic illustration of the invention and the use thereof.

As may be seen in FIG. 1, a conventional defibrillator includes hand-held electrode paddles 12 having switches $S_3$ which must be simultaneously closed in order to apply a defibrillation energy pulse transthoracically to the patient whose heart is in ventricular fibrillation. With switch $S_4$ closed, closing of switches $S_3$ allows discharge of capacitor C and flow of defibrillating current $I_2$ through a circuit including the transthoracic resistance $R_{ext}$ of the patient. $L_2$ and $R_2$, respectively, represent the internal inductance and resistance parameters of the defibrillator. Additionally, the standard defibrillator includes a circuit for charging capacitor C, such indicated as high voltage charging circuit 14 in FIG. 1. FIG. 1 also discloses a current sensing transformer $T_2$ connected to sample and hold circuit 80 and an appropriate voltage divider so that the transthoracic resistance $R_{ext\ 2}$ during the shock may be computed as the quotient of the voltage $V_2$ between the hand-held electrode paddles 12 divided by the sampled peak defibrillating current $I_2$. As may be seen in FIG. 1, A/D converter 30 and microprocessor 40 are used to facilitate calculation of transthoracic resistance and delivered energy during such defibrillation, much as suggested by Jones et al. supra.

According to practice of the invention, the operator will select a desired peak current to be delivered during defibrillation. The microprocessor will then ensure charging of the capacitor to a voltage sufficient to deliver the selected peak current, with this capacitor voltage being dependent on both the selected peak current and prospectively determined transthoracic resistance. To prospectively determine $R_{ext\ 1}$, a low amplitude (approximately 0.1 milliamp) constant current $I_1$ generator 20 provides a pulse of current at some fixed frequency in the range of 20/60 kHz, which by closing switches $S_1$ and $S_3$, is passed through paddles 12 via the patient's thorax prior to discharge of capacitor C. A response voltage $V_1$ is developed across paddles 12 which is proportional to the product of the transthoracic resistance $R_{ext\ 1}$ and the sampled applied current $I_1$. Sensing current $I_1$ via transformer $T_1$ and measuring the response voltage $V_1$, allows a calculated transthoracic resistance $R_{ext\ 1}$ to be obtained by passing the sampled sensed current and voltage through A/D converter 30 then to a microprocessor 40 in which the calculation is performed. Since transthoracic load is predominantly resistive, it may be appreciated that the computed or calculated transthoracic resistance $R_{ext\ 1}$ may then be used, along with the selected peak current to compute the voltage to which the capacitor (C) is charged in order to deliver preselected quantity of peak current to the patient.

With switch $S_2$ set to AUTO (for automatic) microprocessor 40 controls switches $S_1$ and $S_4$ and high voltage charger 14 such that, upon placing the paddles 12 upon the chest of the patient and depressing switches $S_3$, switch $S_1$ will be closed to apply the exploration current $I_1$ across the patient's chest. Prior to, during, or after measurement of transthoracic resistance, high voltage charger 14 commences to charge capacitor C. After calculating $R_{ext\ 1}$, microprocessor 40, directly or indirectly, opens switch $S_1$ and immediately controls the amount of voltage to which capacitor C is charged so that it will deliver to the patient the preselected (by the operator) peak defibrillating current $I_2$. Upon capacitor C being charged to a voltage sufficient to provide the preselected level of peak current $I_2$, microprocessor 40, directly or indirectly, will (automatically) close switch $S_4$ for consequent defibrillation of the patient. The operator may wish sometimes to apply standard defibrillator operation, i.e., setting of a particular energy level, e.g., in joules, for some particular patient and such is permitted by setting switch $S_2$ to manual.

A display 60 and recording device 70 allow display and recordation of important defibrillation parameters such as: the transthoracic resistance $R_{ext\ 1}$ calculated from the exploration current $I_1$; the transthoracic resistance $R_{ext\ 2}$ computed during defibrillation of the patient; the measured level of peak defibrillating current $I_2$ delivered and the delivered energy.

Figure 2:
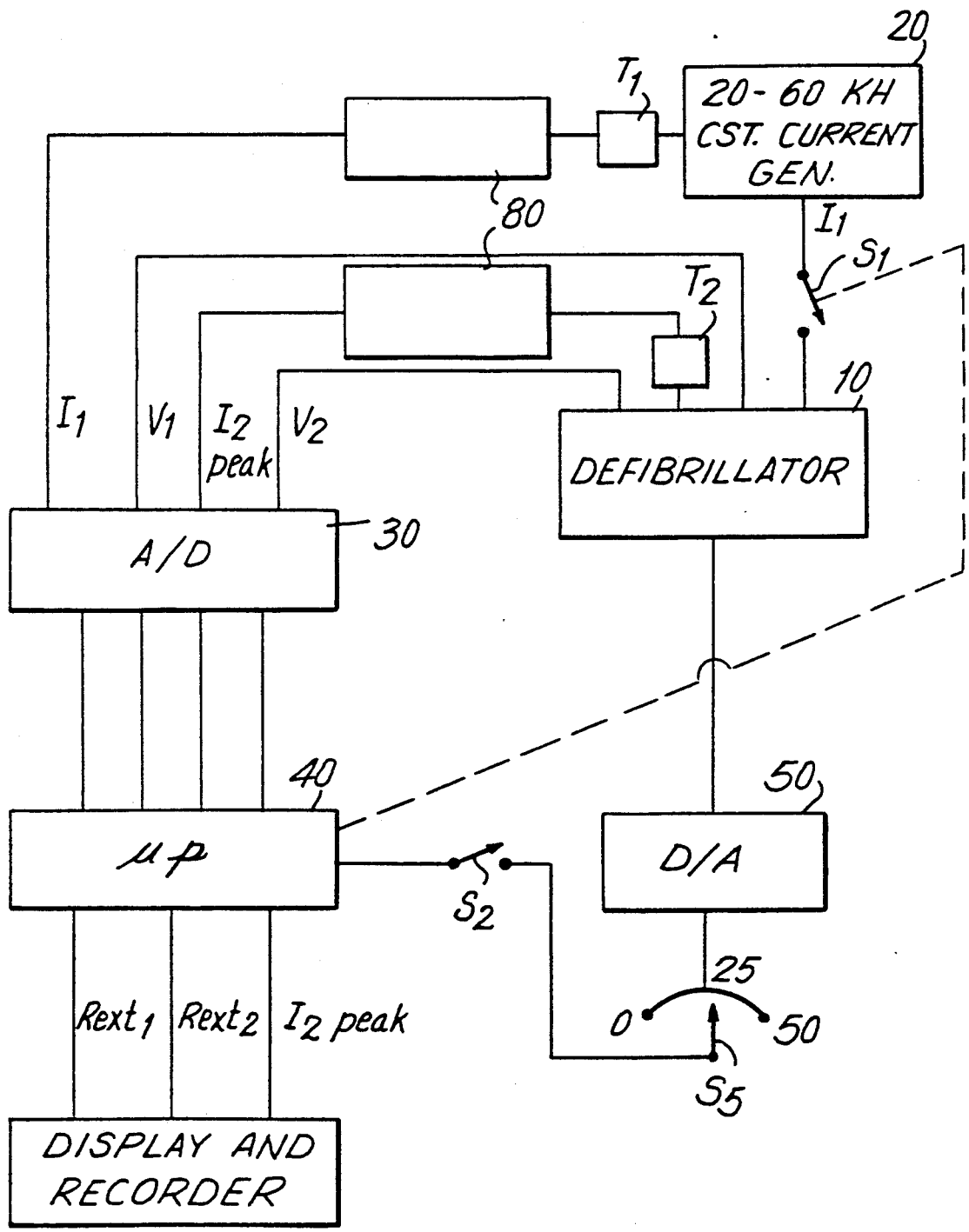
FIG. 2 is a block diagram illustating a standard defibrillator and the add-on components utilized in practice of the instant invention.

FIG. 2 is a block diagram generally illustrating the add-on components used with a standard defibrillator 10 for practice of the present invention. Like numerals have been used for like components throughout the drawings. As can be seen, the modification requires the addition of constant current generator 20 and circuitry for sensing and converting exploration current $I_1$, and voltage $V_1$ as well as defibrillating current $I_2$ and voltage $V_2$ for use by microprocessor 40 which is also added. In the automatic mode ($S_2$ closed), microprocessor 40 controls the operation of switch $S_1$ to apply the expoloration current and through digital/analog converter 50 controls the charging of the defibrillator capacitor (not shown) to a voltage determined by the current, selected by $S_5$, and the resistance calculated from $V_1$ and $I_1$. When the proper voltage is reached the defibrillating pulse is delivered under control of microprocessor 40. It is also contemplated that the microprocessor can be programmed such that the operator may choose to use the defibrillator 10 in its standard or energy-based mode and that the capacitor will be charged to the selected energy. As can be seen, the operation of the modified apparatus is in all respects the same as that of the apparatus shown in FIG. 1.

Just as 200 joules has been used heretofore as an experience—determined energy level for initial defibrillator shock, approximately 25 amperes of peak defibrillation current has been preselected in practice of this invention. This value is based upon limited human patient experience and some change up or down therein may be required with increased human patient experience. As a practical matter, it is proposed that the operator will be able to select from approximately 1-50 peak amperes. Providing a range of selectable currents also permit treatment of arrhythmias other than ventricular fibrillation such as e.g., ventricular tachyardia. Thus, for patients of high transthoracic resistance, defibrillating with 100 joules may apply too low a level of peak defibrillating current. Alternatively, guideline recommended energy levels of 200 joules can provide unnecessarily high peak currents to patients of low transthoracic resistance. Application of some fixed level of peak current to all patients is clearly an improvement for eliminating current variation patient-to-patient.

While the invention has been described with reference to particular embodiments, numerous variations will be obvious to those skilled in the art. Such variations are within the scope of the invention as defined in the claims appended hereto.

I claim:

1. A method of treatment of a patient in ventricular fibrillation, ventricular tachycardia, or supraventricular tachycardia, using a resistance, inductance, capacitance discharge pulse and comprising the steps of:
   selecting a particular peak current level suitable for said treatment;
   applying a low amplitude exploration current from electrodes forming part of a defibrillating apparatus applied to the chest of said patient and sensing a response voltage developed thereby between said electrodes;
   calculating an explored transthoracic resistance from said exploration current and response voltage; and
   charging a discharge capacitor of said defibrillating apparatus, based on said selected peak current and explored transthoracic resistance, sufficiently to create a capacitor discharge voltage generative of said selected peak current level, and thereafter discharging said capacitor through said resistance and inductance via said electrodes thereby delivering said selected peak current for treatment of said patient.

2. A method as in claim 1 further comprising the steps of:
   calculating actual transthoracic resistance and delivered energy from delivered peak discharge current and sensed voltage developed by said peak discharge current between said electrodes applied to the chest of the patient; and
   displaying the values of peak discharge current, delivered energy, and said explored and actual transthoracic resistance.

3. A method as in claim 1, and further comprising the steps of:
   providing said defibrillating apparatus with operator controls calibrated according to current in order to effect selection of said peak current level.

4. A method as in claim 1, wherein said suitable peak current level for ventricular fibrillation is in a range of about 20-50 amperes and for other arrhythmias in the range of approximately 1-50 amperes.

5. A method as in claim 1 further comprising the steps of:
   calculating actual transthoracic resistance from delivered peak discharge current and sensed voltage between electrodes applied to the chest of the patient; and
   charging said discharge capacitor based on said selected peak current level and said actual transthoracic resistance sufficiently to create a capacitor discharge voltage generative of said selected peak current level, thereby enabling successive discharges of said discharge capacitor to deliver said selected peak current.

6. A method as in claim 5 wherein a different peak current level is selected for said successive discharges.

7. In an apparatus for treatment of a patient having ventricular fibrillation, ventricular tachycardia or supraventricular tachycardia by delivering a resistance, inductance, capacitance discharge pulse through electrodes applied to the chest of said patient, the improvement comprising:
   selection means for selecting a particular peak current level suitable for said treatment;
   current generating means connectable to electrodes for generating a low amplitude exploration current through said electrodes when applied to the chest of a patient
   sensing means for measuring said exploration current and for measuring a response voltage developed between said electrodes by said exploration current;
   computing means connected to said selection means, said current generating means and said sensing means for applying said exploration current and calculating explored transthoracic resistance from said exploration current and said voltage;
   charging means connected to said computing means and connectable to a discharge capacitor for charging said capacitor based on said selected peak current level and said calculated explored transthoracic resistance sufficiently to create a discharge pulse generative of said selected peak current level; and means connected to said computing means and said electrodes for applying said discharge pulse to said patient thereby delivering said selected peak current for said treatment.

8. The improved apparatus of claim 7 further comprising;

sensing means connected to said computing means for measuring delivered peak current and for measuring the response voltage developed between said electrodes by said delivered peak current;

said computing means calculating transthoracic resistance from said delivered peak current and said response voltage between electrodes applied to the chest of the patient; and charging said capacitor based on said selected peak current and said calculated transthoracic resistance sufficiently to create a discharge pulse generative of said selected peak current level.

9. The improved apparatus of claim 7 further comprising:

energy selection means for selecting pulse energy in units of joules or watt-seconds, and for causing said computer means to control said charging means to charge said capacitor sufficiently to create a discharge pulse generative of said selected energy; and further selection means for selecting either said energy selecting means or said means for selecting a particular peak current level.

* * * * *